(12) United States Patent
Sipinski et al.

(10) Patent No.: US 7,893,829 B2
(45) Date of Patent: Feb. 22, 2011

(54) DEVICE THAT INCLUDES A MOTION SENSING CIRCUIT

(75) Inventors: Gene Sipinski, Elgin, IL (US); Thomas P. Blandino, Cottage Grove, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 358 days.

(21) Appl. No.: 12/157,705

(22) Filed: Jun. 12, 2008

(65) Prior Publication Data
US 2009/0309717 A1 Dec. 17, 2009

(51) Int. Cl.
G08B 21/00 (2006.01)
G01J 5/00 (2006.01)
(52) U.S. Cl. ............... 340/540; 340/555; 250/338.1
(58) Field of Classification Search ............ 340/500, 340/517, 518, 540, 541, 555, 556, 557; 128/200.14, 128/200.16; 250/208.1, 338.1; 310/317; 4/323
See application file for complete search history.

(56) References Cited

U.S. PATENT DOCUMENTS

| | | | |
|---|---|---|---|
| 3,813,540 A | 5/1974 | Albrecht | |
| 4,063,664 A | 12/1977 | Meetze, Jr. | |
| 4,462,670 A | 7/1984 | Maida | |
| 4,736,097 A | 4/1988 | Philipp | |
| 4,830,791 A | 5/1989 | Muderlak et al. | |
| 4,973,833 A | 11/1990 | Takada et al. | |
| 5,015,994 A | 5/1991 | Hoberman et al. | |
| 5,397,028 A * | 3/1995 | Jesadanont | 222/1 |
| 5,699,243 A | 12/1997 | Eckel et al. | |
| 5,895,986 A | 4/1999 | Walters et al. | |
| 5,946,209 A | 8/1999 | Eckel et al. | |
| 6,050,016 A | 4/2000 | Cox | |
| 6,151,529 A | 11/2000 | Batko | |
| 6,264,548 B1 | 7/2001 | Payne, Jr. et al. | |
| 6,390,453 B1 | 5/2002 | Frederickson et al. | |
| 6,554,203 B2 | 4/2003 | Hess et al. | |
| 6,593,701 B1 | 7/2003 | Hsieh | |
| 6,722,529 B2 | 4/2004 | Ceppaluni et al. | |
| 6,888,323 B1 | 5/2005 | Null et al. | |
| 7,339,471 B1 | 3/2008 | Chan et al. | |
| 7,355,349 B2 | 4/2008 | Evans | |
| 7,554,084 B2 * | 6/2009 | Mok et al. | 250/338.1 |
| 7,723,899 B2 * | 5/2010 | Blandino et al. | 310/317 |

(Continued)

FOREIGN PATENT DOCUMENTS

EP 038 598 10/1981

(Continued)

OTHER PUBLICATIONS

International Search Report and Written Opinion dated Dec. 16, 2009 Appl. No. PCT/US2009/003453.

*Primary Examiner*—Van T. Trieu

(57) ABSTRACT

A dispensing device includes a dispenser configured to dispense a volatile material, a sensor configured to detect an environmental condition, and a nonlinear circuit element coupled to the sensor to establish a bias point. A voltage level at the bias point varies nonlinearly with respect to a current that flows through the sensor, wherein the current that flows through the sensor represents the environmental condition. The dispensing device further includes a controller coupled to the bias point. The controller controls the dispenser to dispense the volatile material in response to the environmental condition.

20 Claims, 5 Drawing Sheets

U.S. PATENT DOCUMENTS

2007/0017505 A1* 1/2007 Lipp et al. ............ 128/200.16
2007/0046143 A1 3/2007 Blandino et al.
2008/0116356 A1* 5/2008 Mok et al. ............... 250/208.1
2010/0139652 A1* 6/2010 Lipp et al. ............ 128/200.14

FOREIGN PATENT DOCUMENTS

| | | |
|---|---|---|
| GB | 2 248 888 | 4/1992 |
| WO | 9310910 A | 6/1993 |
| WO | 9630726 A | 10/1996 |

* cited by examiner

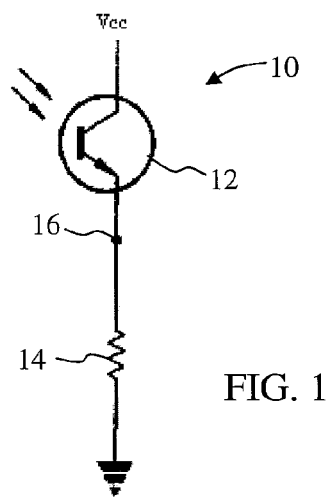
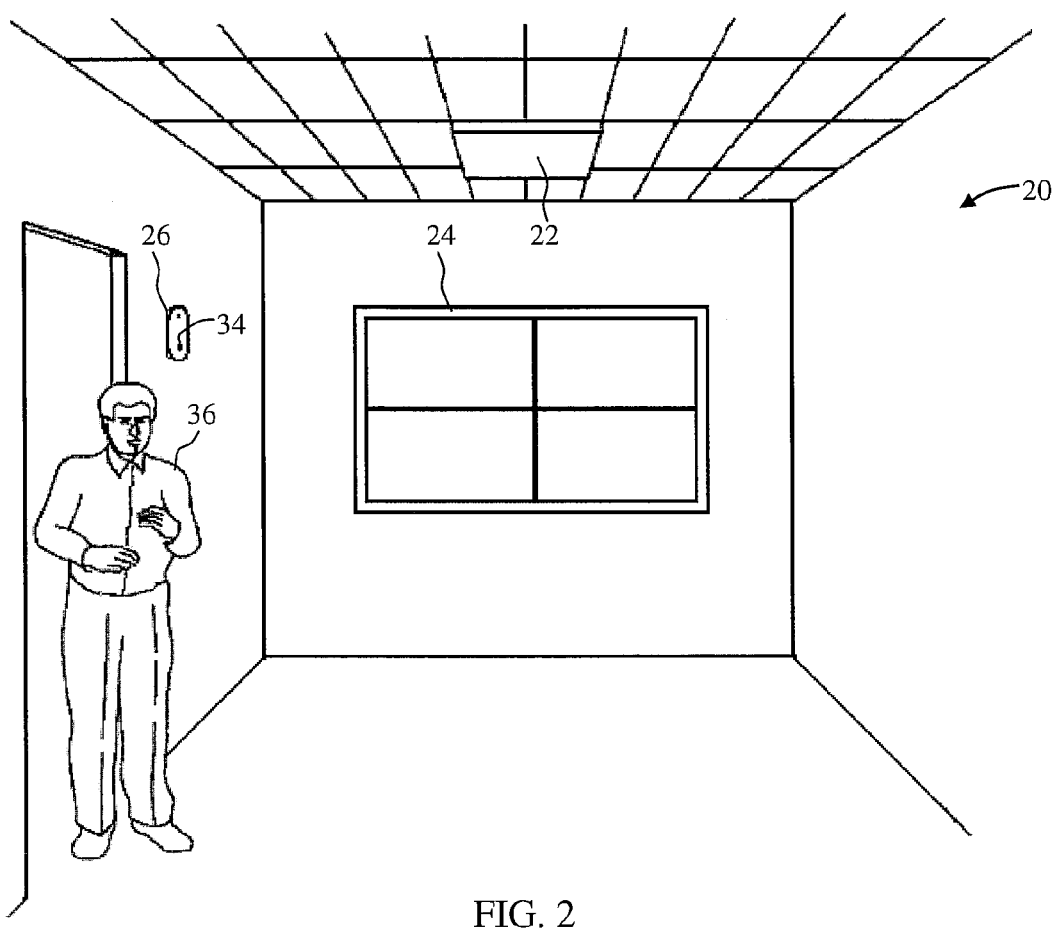
FIG. 1
FIG. 2

DEVICE THAT INCLUDES A MOTION SENSING CIRCUIT

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates generally to devices with sensors and, more particularly, to devices that dispense volatile materials in response to detection of an environmental condition.

2. Description of the Background of the Invention

Diffusion devices or dispensers are used to dispense volatile materials, such as perfumes, deodorizers, insecticides, insect repellants, and the like. Many such devices are passive diffusion devices that require only ambient air flow to dispense the volatile material, while other devices are active diffusion devices. Active diffusion devices are found in a variety of forms, some include fans and/or heaters to aid in the dispersal of volatile materials, others actuate a valve stem of an aerosol container to dispense a volatile material contained therein, still others utilize an ultrasonic transducer to break up a liquid volatile material into droplets that are ejected from the device, and yet others include any combination of the above or any other known type of active diffusion device. Various examples of such devices can be found in Helf et al. U.S. patent application Ser. No. 11/401,572, Beland et al. U.S. patent application Ser. No. 11/801,554, Helf et al. U.S. patent application Ser. No. 11/893,456, Helf et al. U.S. patent application Ser. No. 11/893,476, Helf et al. U.S. patent application Ser. No. 11/893,489, Helf et al. U.S. patent application Ser. No. 11/893,532, Schwarz U.S. patent application Ser. No. 11/341,046, Sipinski et al. U.S. patent application Ser. No. 12/080,336, and Pedrotti et al. U.S. Pat. No. 6,917,754, all of which are incorporated herein by reference in their entireties. Further, some active diffusion devices include a sensor to detect motion or light in a space, wherein such devices dispense a volatile material in response to signals from the sensor.

Early diffusion devices that included sensors were developed for use in restrooms to dispense perfumes or deodorizers to combat malodors in the restroom. However, when a need arose for such devices in other environments, e.g., a living room, an office space, an outdoor area, etc., prior art devices that were developed for use in the restroom were found to be unsatisfactory. More specifically, the prior art devices were designed to operate in a relatively small space in which ambient light conditions were relatively low and generally stable. Consequently, the sensors of such prior art devices were only configured to function in a narrow range of operating conditions.

Referring to FIG. 1, a basic prior art sensor configuration 10 is depicted that includes a phototransistor 12. A collector electrode of the phototransistor 12 is coupled to a supply voltage level Vcc and an emitter electrode of the phototransistor 12 is coupled via a resistor 14 to a ground voltage level. Varying light levels that reach the phototransistor 12 result in variations in current that flows through the phototransistor 12. The varying current results in a varying voltage level at a bias point 16 that is established at a junction between the phototransistor 12 and the resistor 14. More specifically, the combination of the phototransistor 12 and the resistor 14 results in a linear relationship between the current through the phototransistor 12 and the voltage level at the bias point 16. The voltage level at the bias point 16 is monitored to trigger a motion detect signal, wherein fluctuations in the voltage level at the bias point 16 are interpreted by a controller (not shown) to determine if motion has been sensed by the phototransistor 12, i.e., the variation in light level is interpreted by the controller as motion. Thereafter, the controller is typically configured in such prior art devices to activate a dispensing mechanism to dispense a volatile material into the atmosphere if motion has been sensed.

When such prior art devices are placed in larger spaces with high ambient light conditions, the sensors of the prior art devices do not function properly to detect motion. For example, when a prior art device that incorporates the sensor configuration 10 of FIG. 1 is placed in a living room with high levels of ambient light (see generally FIG. 2), the ambient light in the living room causes a high current to flow through the phototransistor 12. The high current that flows through the phototransistor 12 results in a high voltage level at the bias point 16 because of the linear relationship between the current through the phototransistor 12 and the voltage at the bias point 16. In some cases, the high voltage level approaches the voltage level of the supply voltage. Consequently, a controller coupled to the bias point 16 will have difficulty determining if motion has been sensed based on fluctuations in the voltage level at the bias point. Similarly, in low ambient light conditions, a low current flows through the phototransistor 12 that results in a low voltage level at the bias point 16 that can approach the ground voltage level. In such low ambient light conditions the controller coupled to the bias point 16 similarly has difficulty determining if motion has been sensed. This is because the sensitivity of the sensor configuration 10 is directly and linearly proportional to the ambient light level. Therefore, devices that incorporate the sensor configuration 10 of FIG. 1 often do not have enough sensitivity to operate in a wide range of environments, such as in high and low ambient light conditions.

Further, prior art sensor configurations suffer from an inability to detect motion at substantial distances. For example, in high ambient light conditions, only motion very close to the phototransistor 12 will trigger a motion detect signal. Therefore, motion in portions of the room away from the phototransistor 12 will not trigger a motion detect signal.

Another problem that affects the performance of the prior art devices is the issue of false triggers due to high frequency and low frequency environmental conditions that should be ignored but, instead, are interpreted as the detection of motion in a room. For example, a high frequency condition is the flickering of a fluorescent light in a room (see generally FIG. 2), which will be interpreted as the detection of motion in some prior art devices. Further, a low frequency condition can be a transition in ambient light from afternoon to evening by the setting of the sun through a window of a room (see generally FIG. 2). Likewise, such low frequency light changes can also be interpreted as the detection of motion in some prior art devices. Therefore, there is a need for a dispensing device that solves the various issues discussed hereinabove.

SUMMARY OF THE INVENTION

According to one embodiment, a dispensing device includes a dispenser configured to dispense a volatile material, a sensor configured to detect an environmental condition, and a nonlinear circuit element coupled to the sensor to establish a bias point. A voltage level at the bias point varies nonlinearly with respect to a current that flows through the sensor, wherein the current that flows through the sensor represents the environmental condition. The dispensing device further includes a controller coupled to the bias point. The controller controls the dispenser to dispense the volatile material in response to the environmental condition.

According to another embodiment, a dispensing device includes a dispenser configured to dispense a volatile material, a phototransistor, and a diode coupled to the phototransistor to establish a bias point. A voltage level at the bias point varies nonlinearly with to the bias point to attenuate high and low frequency conditions and a controller is coupled to the bias point via the band-pass filter. The controller controls the dispenser to dispense the volatile material in response to a fluctuation in the voltage level at the bias point.

In a further embodiment, a method of dispensing a volatile material includes the steps of detecting an environmental condition with a photocell and coupling a nonlinear circuit element to the photocell to establish a bias point therebetween. A voltage level at the bias point varies nonlinearly with respect to a current that flows through the photocell. The method further includes the step of dispensing a volatile material in response to a transition in the voltage at the bias point.

Other aspects and advantages of the present invention will become apparent upon consideration of the following detailed description.

BRIEF DESCRIPTION OF THE DRAWINGS

FIG. 1 is schematic diagram of a prior art embodiment of a sensor configuration;

FIG. 2 is a general view of a room in which a dispensing device is placed;

DETAILED DESCRIPTION OF THE DRAWINGS

Figure 3:
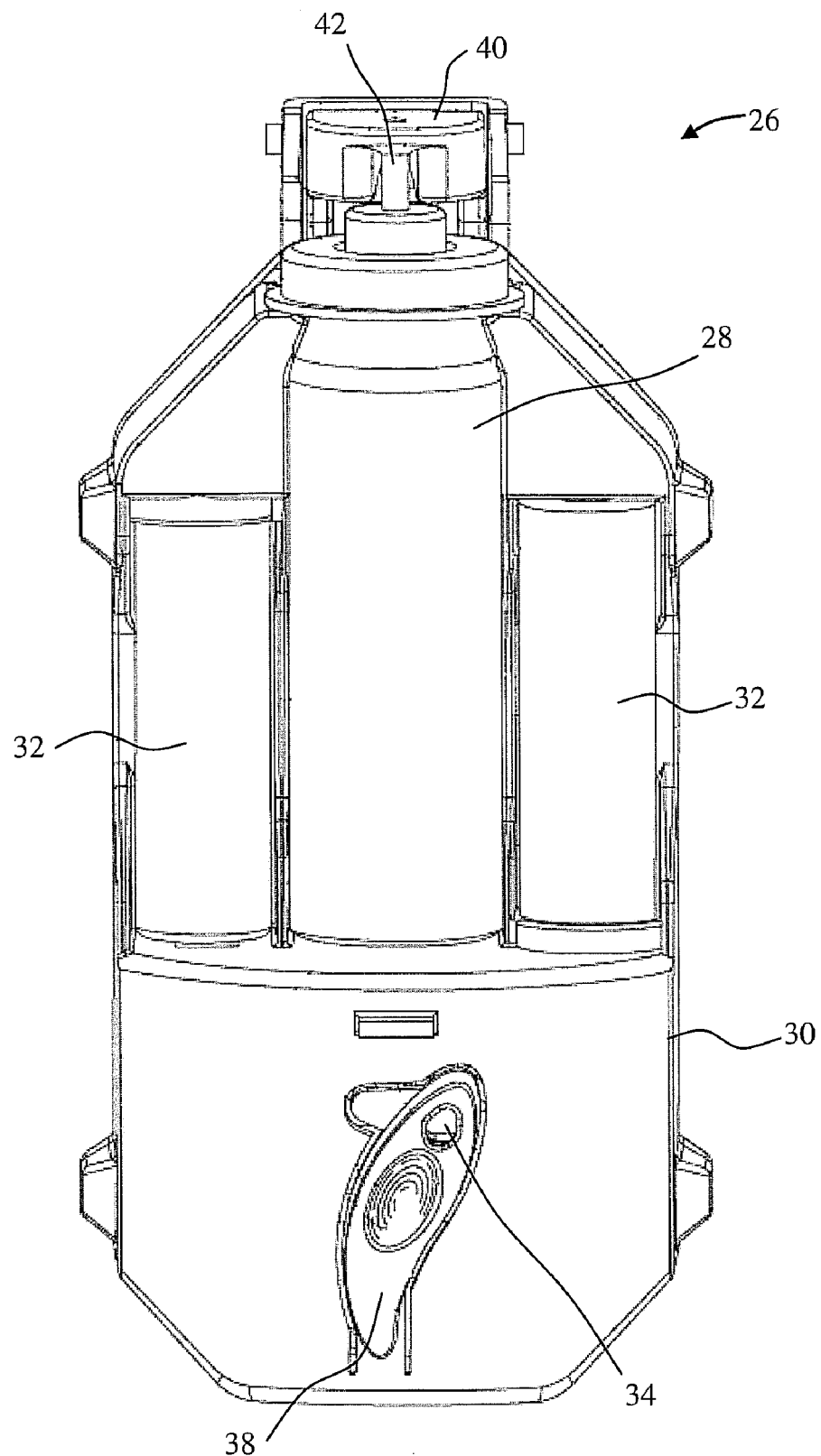
FIG. 3 is an isometric view of a dispensing device according to a first embodiment.

FIG. 2 illustrates a room 20 that includes a fluorescent light source 22 and a window 24 through which sunlight enters the room 20. A device 26 is positioned within the room 20 and is illustrated with greater particularity in FIG. 3. The device 26 is adapted to dispense the contents of an aerosol container 28 and is preferably one of the devices described in Carpenter et al. U.S. patent application Ser. No. 11/725,402, which is incorporated herein by reference in its entirety. The device 26 includes a housing 30 that is adapted to receive the aerosol container 28 and batteries 32. The device 26 also includes a sensor, such as a phototransistor 34, which detects changes in the ambient light conditions within a sensory path thereof. In the present embodiment, detected changes in the ambient light level, e.g., from a person 36 entering the room 20 and crossing the sensory path of the phototransistor 34, are representative of motion within the vicinity of the device 26 and cause a signal to be generated by the phototransistor 34 to initiate an activation sequence or spray operation of the device 26, which will be described in detail below. FIG. 3 also illustrates that the device 26 includes a pushbutton 38, an actuator arm 40 for depressing a valve stem 42 of the aerosol container 28, and a light emitting diode ("LED") (not shown in FIG. 3). In the present embodiment, the LED is generally positioned behind the pushbutton 38 to illuminate a portion thereof.

Figure 4:
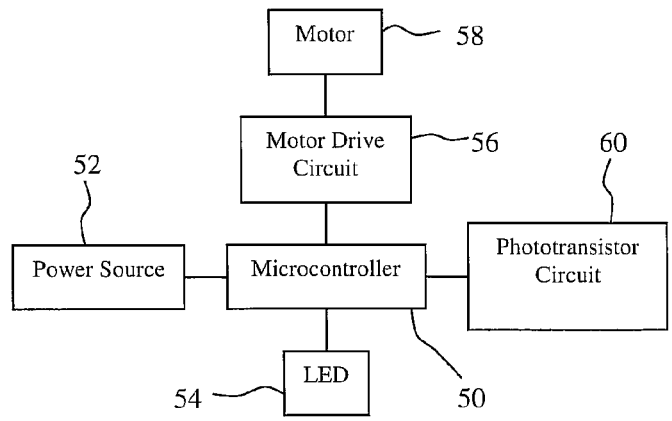
FIG. 4 is a block diagram of circuitry for controlling the dispensing device of FIG. 3.
Figure 5:
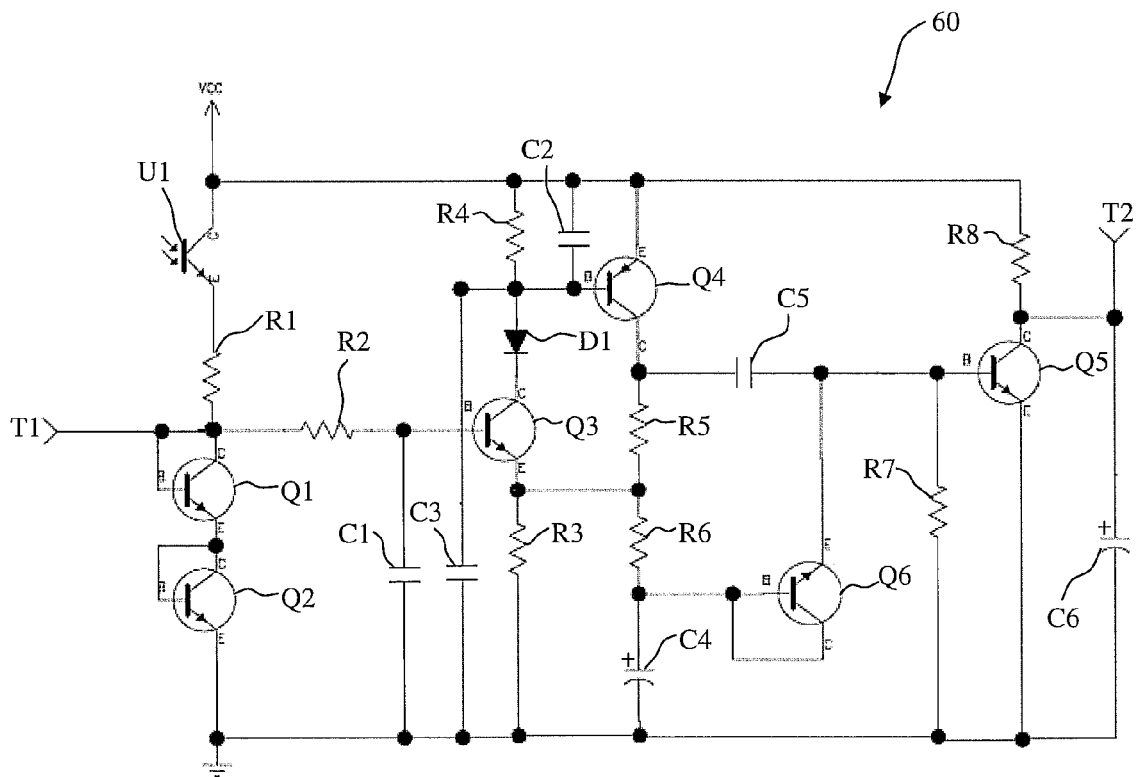
FIG. 5 is a schematic diagram of a phototransistor circuit for use with the dispensing device of FIG. 3.

The device 26 also includes circuitry within the housing 30, which is depicted in FIGS. 4 and 5. Referring to FIG. 4, the circuitry that controls the device 26 includes a microcontroller 50, a power source 52, an LED 54, a motor drive circuit 56 that drives a motor 58, and a phototransistor circuit 60. In one embodiment, the microprocessor 50 may be a SH6610C or a SH66P51 4-bit micro-controller, such as those manufactured by Sino Wealth Microelectronics Corp. Ltd., of 3301, 33/F, Skyline Tower, 39 Wang Kwong Road, Kowloon Bay, Hong Kong. It is also contemplated that other types of programmable elements may be alternatively or additionally used, e.g., an integrated circuit, which may comprise an application specific integrated circuit (ASIC), may be used in any of the described embodiments. Further, in the present embodiment, the power source 52 includes one or more AA batteries. However, in other embodiments, the power source 52 can be any other suitable power source as would be apparent to one of ordinary skill in the art. The microcontroller 50 is configured to drive the LED 54 to emit light. For example, in various embodiments, the LED 54 is driven to emit light when the device is initialized, before the device dispenses a volatile active, to indicate an operating mode, etc., as would be apparent to one of ordinary skill in the art. Further, the microcontroller 50 is configured to control the motor drive circuit 56 in response to signals from the phototransistor circuit 60. More specifically, the microcontroller 50 controls the motor drive circuit 56 to drive the motor 58 to actuate the actuator arm 40 (see FIG. 3). In other embodiments, the microcontroller 50 can be configured to drive other circuitry, e.g., a piezoelectric device, a fan, a heater, and any other circuitry as would be apparent to one skilled in the art.

Referring to FIG. 5, the phototransistor circuit 60 includes a phototransistor U1. A collector electrode of the phototransistor U1 is coupled to a supply voltage Vcc and an emitter electrode is coupled to a first terminal of a resistor R1. A second terminal of the resistor R1 is coupled to one or more non-linear circuit elements. In this embodiment, the phototransistor circuit 60 includes two non-linear circuit elements, i.e., first and second transistors Q1 and Q2, which are used to obtain twice the output at the bias point T1 so that less amplification is required and to provide a suitable DC voltage level to a transistor Q3, described in greater detail below. The electrodes of the transistors Q1, Q2 are connected together to form diodes. More particularly, the second terminal of the resistor R1 is coupled to a collector electrode of the first transistor Q1 and a base electrode of the first transistor is coupled to the collector electrode. An emitter electrode of the first transistor Q1 is coupled to a collector electrode of the second transistor Q2 and a base electrode of the second transistor is coupled to the collector electrode. An emitter electrode of the second transistor Q2 is coupled to ground. In other embodiments, other known non-linear circuit elements can be utilized, such as ordinary or specialized diodes.

In the present embodiment, a bias point T1 is established at a junction between the second terminal of the resistor R1 and the collector electrode of the first transistor Q1. Due to the exponential I-V characteristic of the first and second transistors Q1, Q2, respectively, the voltage at the bias point is proportional to the logarithm of the current $I_P$ flowing through the phototransistor U1, wherein the current $I_P$ is proportional to the amount of light that reaches the phototransistor U1. Thus, the phototransistor circuit 60 can operate over a wide range of ambient light conditions, because the range of current values that result from the wide range of ambient light conditions is converted into a smaller, logarithmically-related voltage range at the bias point T1. Further, the voltage level at the bias point T1 is maintained at a relatively stable level between the supply voltage and ground to provide a maximum range of variation for the current $I_P$ through the phototransistor T1.

The voltage level at the bias point T1 is thereafter filtered to attenuate unwanted high and low frequency conditions and sent through amplification stages to amplify the voltage level. The resulting filtered and amplified voltage level is then supplied to the microcontroller 50 as a detect signal. The microcontroller is configured to interpret fluctuations in the detect signal as motion detected by the phototransistor U1 and to control the motor drive circuit 56 in accordance with such motion.

Referring again to FIG. 5, the filtering is accomplished by high-pass and low-pass filters, which in combination form a band-pass filter to attenuate unwanted high and low frequency conditions. As would be apparent to one of ordinary skill in the art, the cut-off frequencies of the high-pass and low-pass filters are adjustable to obtain the desired band-pass range for the overall circuit.

Further, the amplification stages in the present embodiment include transistor stages. However, in other embodiments, other types of amplification stages can be used, such as operational amplifiers, as would be apparent to those of skill in the art. More specifically, in FIG. 5, a first electrode of a resistor R2 is coupled to the bias point T1 and a second electrode of the resistor R2 is coupled via a capacitor C1 to ground. The resistor R2 and capacitor C1 form a first low-pass filter. The cut-off frequency of the low-pass filter can be set by adjusting the resistance of the resistor R2 and/or the capacitance of the capacitor C1, as would be apparent to one of ordinary skill in the art. The second electrode of the resistor R2 is also coupled to a base electrode of a transistor Q3. A collector electrode of the transistor Q3 is coupled to a cathode of a diode D1 and an emitter electrode of the transistor Q3 is coupled via a resistor R3 to ground. An anode of the diode D5 is connected via a resistor R4 to the supply voltage Vcc. A capacitor C2 is coupled in parallel with the resistor R4 from the supply voltage Vcc to the anode of the diode D1. In addition, a first electrode of a capacitor C3 is also coupled to the anode of the diode D1, wherein a second electrode of the capacitor C3 is coupled to ground. The resistor R4 and capacitors C2 and C3 form a second low-pass filter. Further, the anode of the diode D1 is also coupled to a base electrode of a transistor Q4, wherein an emitter electrode of the transistor Q4 is coupled to the supply voltage Vcc and a collector electrode of the transistor Q4 is coupled via a resistor R5 to the emitter electrode of the transistor Q3. The emitter electrode of the transistor Q3 is further coupled to a first electrode of a resistor R6, wherein a second electrode of the resistor R6 is coupled via a polarized capacitor C4 to ground. The resistors R5 and R6 establish an AC circuit gain. Further, the resistor R5 and the capacitor C4 form a first high-pass filter. Referring back to the transistor Q4, the collector electrode thereof is further coupled to a first electrode of a capacitor C5, wherein a second electrode of the capacitor C5 is coupled to a base electrode of a transistor Q5. In addition, a resistor R7 is coupled between the second electrode of the capacitor C5 and ground. The resistor R7 and the capacitor C5 form a second high-pass filter and also function as a DC blocking circuit to pass a signal to the transistor Q5. It should be generally noted that the cut-off frequencies of any of the high-pass filters can be set by adjusting the resistances and/or capacitances thereof, as would be apparent to one of ordinary skill in the art. Referring again to the transistor Q5, same acts as a threshold detector that switches on when the signal from the second high-pass filter equals one emitter-base voltage drop. A collector electrode of the transistor Q5 is further coupled via a resistor R8 to the supply voltage Vcc and an emitter electrode of the transistor Q5 is coupled to ground. A polarized capacitor C6 is coupled in parallel across collector and emitter electrodes of the transistor Q5. In addition, a transistor Q6 is coupled between the second electrode of the capacitor C5 and a junction between the resistor R6 and the capacitor C4. The transistor Q6 is configured as a diode, wherein a collector electrode thereof is connected to a base electrode thereof. The base electrode of the transistor Q6 is further coupled to the junction between the resistor R6 and the capacitor C4 and an emitter of the transistor Q6 is coupled to the second electrode of the capacitor C5. The transistor Q6 and the emitter-base junction of the transistor Q5 act as clamping circuits, which change the cutoff frequency of the second high-pass filter so that the circuit recovers quickly from large changes in light. In particular, the transistor Q6 reacts to signals caused by decreases in light and the transistor Q5 reacts to signals caused by increases in light. The detect signal is established at a junction T2 between the resistor R8 and the collector electrode of the transistor Q5. The detect signal is supplied to the microcontroller 60 and interpreted to determine whether the phototransistor U1 has detected motion, as noted above.

Figure 6:
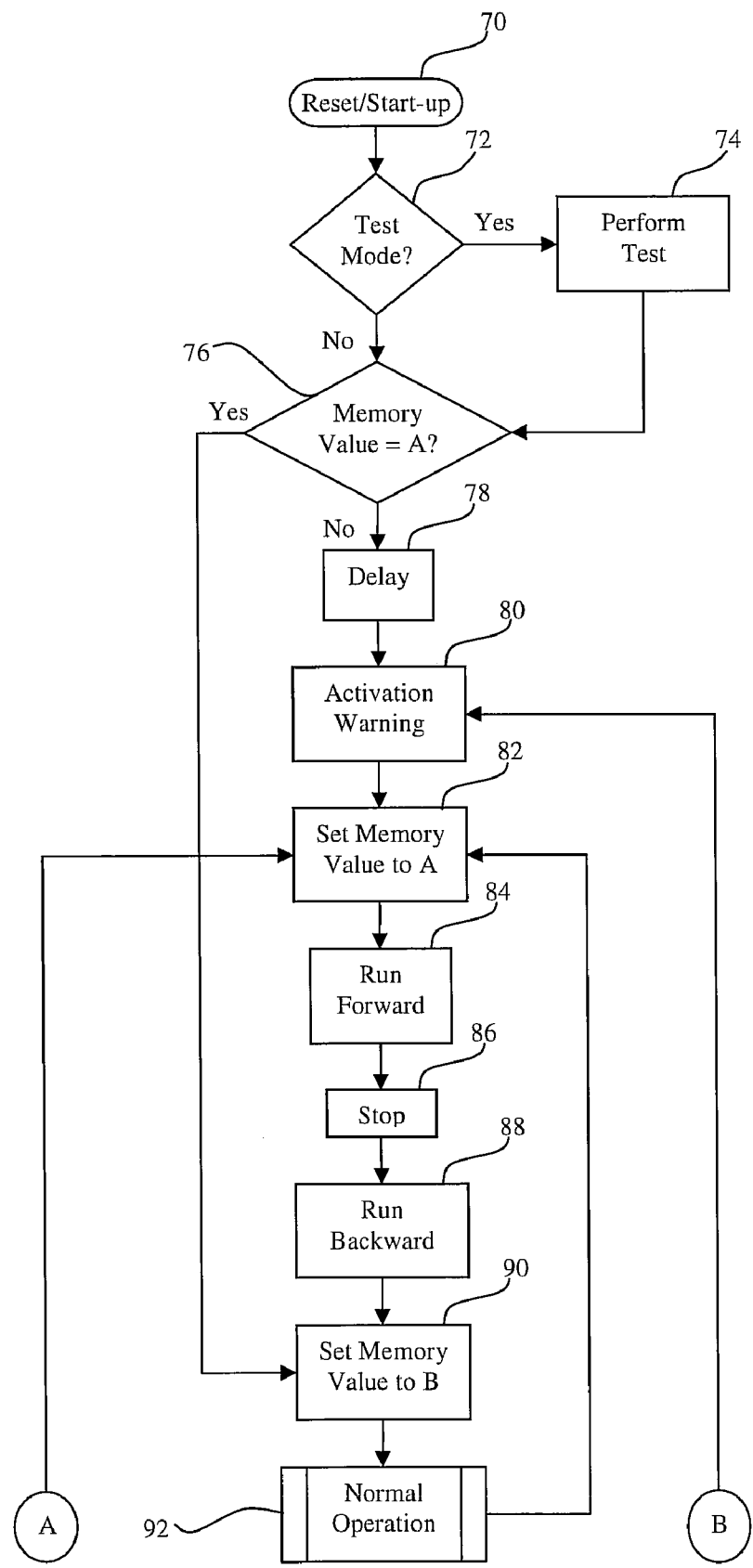
FIG. 6 is a flowchart that illustrates programming that may be executed by the dispensing device of FIG. 3.

Referring to FIG. 6, one embodiment of programming implemented by the microprocessor 50 to control the device 26 initiates at a reset/start-up block 70 when the batteries 32 are inserted into the device 26 or when the device 26 experiences a brown-out condition, as will be described in detail hereinbelow. Thereafter, control passes to a decision block 72, which determines whether a test mode is to be performed. If the test mode is to be performed, then the test mode is performed at a block 74. In one embodiment, the test mode is performed at a manufacturing facility to ensure the proper operation of the device 26 before a consumer uses the device 26. For example, the decision block 72 can determine that a test mode is to be performed when batteries 32 are inserted into the device 26 and the pushbutton 38 is depressed for five seconds. Thereafter, various tests can be performed during the block 74, such as testing the LED 54, the motor drive circuit 56 and motor 58, and the phototransistor circuit 60. Other tests can also be performed as would be apparent to one of ordinary skill in the art.

In the present embodiment, control passes to a decision block 76 after the test mode is performed at the block 74 or if the decision block 72 determines that a test mode is not to be performed. The decision block 76 determines whether a specified memory location, e.g., a memory location in the microcontroller 50, stores a value equal to a specified value "A." If the memory value is not equal to "A," then control passes to a delay block 78 and control pauses for a predetermined period of time, e.g., about 10-30 seconds. Following the delay block 78, control passes to a block 80 and a warning or notice is issued that an activation sequence is imminent. In the present embodiment, the warning is a flashing or flickering of the LED 54. However, in other embodiments, the warning can be any combination of a visual, audible, tactile, olfactory, or any other warning that would be apparent to one of ordinary skill in the art. After the block 80, control passes to a block 82 and the memory location is set to the value "A."

Next, the programming performs an activation sequence. In the present embodiment, the activation sequence is a spray operation that includes blocks 84, 86, and 88. More specifically, the spray operation begins at the block 84 where the motor drive circuit 56 is energized to drive the motor 58 in a forward direction to move the actuator arm 40 downwardly to depress the valve stem 42 of the aerosol container 28 into an open position to allow for the emission of a volatile material from the aerosol container 28. The motor drive circuit 56 and motor 58 are deenergized in a block 86. Thereafter, the motor drive circuit 56 is energized to drive the motor 58 in a reverse direction to move the actuator arm 40 in the opposite direction in the block 88 to assist the valve stem 42 in moving to a closed and non-depressed position. In one embodiment, the motor drive circuit 56 is energized during the block 84 for about 1 second, the motor drive circuit 56 is deenergized during the block 86 for about 150 milliseconds, and the motor drive circuit 56 is energized during the block 88 for about 400 milliseconds. Modifications to the activation sequence of the present embodiment can include any sequence of the same or different steps, as would be apparent to one of ordinary skill in the art. Following the activation sequence, control passes to a block 90, during which the memory location is set to a specified value "B," which is different than the value "A" as noted above.

Referring back to the decision block 76, if the specified memory location stores a value equal to the specified value "A," then control bypasses the blocks 78-88 and passes directly to the block 90 to set the memory location to the value "B." After the block 90, control passes to a block 92 and programming enters a normal operational procedure or mode, wherein the programming executes manual or automatic activation sequences, as described in detail below.

In the present embodiment, the programming performs a startup operation that includes execution of the blocks 84-88 to perform an activation sequence when new batteries 32 are inserted into the device 26. The programming also performs activation sequences in accordance with the normal operation mode. During both the start-up and normal operating modes, an increase in current draw occurs when the motor drive circuit 56 is energized to drive the motor 58. This increased current draw results in a voltage drop across the batteries 32 and the associated circuitry powered by the batteries 32, e.g., the microprocessor 50. The increased current draw and additional voltage drop are temporary, i.e., such effects cease after the activation sequence is completed or interrupted.

During the normal operational mode, the batteries 32 provide a sufficient voltage level to the microprocessor 50 that is higher than a threshold operating level for the microprocessor 50 despite the additional voltage drop during the activation sequence. As the battery voltage becomes depleted, the temporary voltage drop will cause the voltage level supplied to the microprocessor 50 to fall below the threshold operating level. When the voltage level supplied to the microprocessor 50 falls below the threshold operating level during an activation sequence, the device 26 enters a brownout state and causes a low voltage reset of the device 26 (see block 70 of FIG. 6) and a re-running of the reset/start-up methodology described above. However, prior to the resetting of the device 26 a fluid may be dispensed during the interrupted activation sequence.

Upon the resetting of the device 26 the programming would normally cause yet another activation sequence to occur (see blocks 78-88), which would thereafter result in another brownout and resetting of the device 26. However, the programming of the present device 26 is capable of identifying a reset caused by a brownout, i.e., a low voltage reset, at the decision block 76 when the value stored in the memory location is determined to be equal to "A," thereby allowing the device 26 to bypass an undesired additional reset activation sequence. Specifically, in the present embodiment the programming sets the memory location to the value "A" at the block 82 when the device 26 is initially turned on. As noted above, a subsequent activation sequence and brownout cause the device 26 to reset during or immediately after the activation sequence, which passes control back to block 70 before control passes to block 90 and the memory value is reset to the value "B." In the present embodiment, the memory in the microcontroller 50 retains the value stored therein during a reset condition but not a power-on condition. Consequently, because the memory location is equal to the value "A," control bypasses yet another activation sequence and immediately passes to the block 90. If the memory location is not equal to the value "A," then the reset was not caused by a brownout or low voltage condition and the programming performs the startup operation that includes the activation sequence. In this manner, the programming illustrated in FIG. 6 can distinguish between a power-on reset and a low voltage reset and modify the operation of the device 26 accordingly.

In the present embodiment, the two fully charged batteries 32 provide about 3.2 volts to the microprocessor 50 and the other electrical or electromechanical components of the device 26. The threshold operating level of the microprocessor 50 is about 1.8 volts. The activation sequence causes about a 0.5-0.6 voltage drop across the batteries 32. Consequently, fully charged batteries 32 provide a sufficient voltage level to the microprocessor 50 even with the voltage drop caused by the activation sequence. However, when the batteries 32 become depleted to within a range of about a 2.2-2.3 volts the additional voltage drop during the activation sequence may temporarily lower the voltage supplied to the microprocessor 50 to around 1.7 volts, thereby causing the microprocessor 50 to reset because of a low voltage condition.

Figure 7:
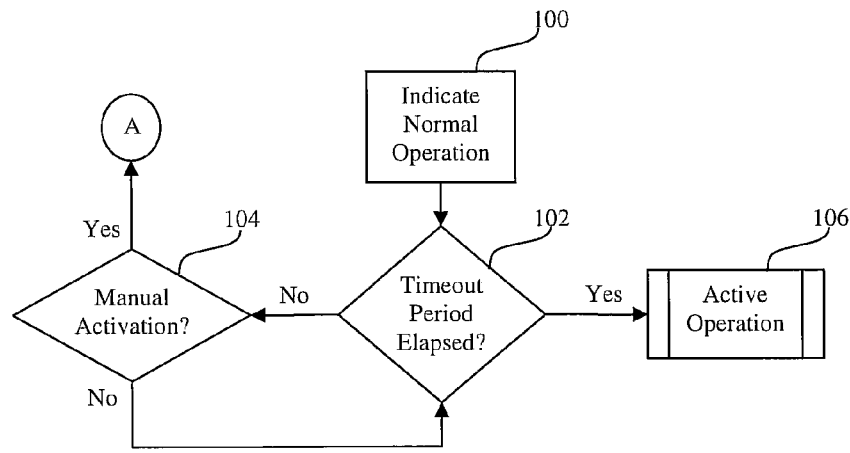
FIG. 7 is a flowchart that illustrates programming that may be executed during a normal operational mode of the dispensing device of FIG. 3.

FIG. 7 illustrates the normal operational mode of the present embodiment, which begins at a block 100. At the block 100 the device 26 turns on the LED 54 to provide an indication that the device 26 is in the normal operational mode. Following the block 100, control passes to a decision block 102 and the programming implements a timeout mode. The timeout mode can last for any period of time, e.g., ten seconds, thirty minutes, one hour, etc. Control remains in the timeout mode without performing an activation sequence unless a decision block 104 determines that the pushbutton 38 has been depressed or until the block 102 determines that the period of time has lapsed. If the pushbutton 38 has been depressed, control loops back to the block 82 where the memory location is set to the value "A" and the activation sequence is performed, as described above. Thereafter, the memory value is set to "B," and the workflow returns to the timeout mode in block 102. If the period of time has lapsed without the pushbutton 38 being depressed, then control passes to a block 106, wherein the programming implements a third or active operational procedure or mode.

Figure 8:
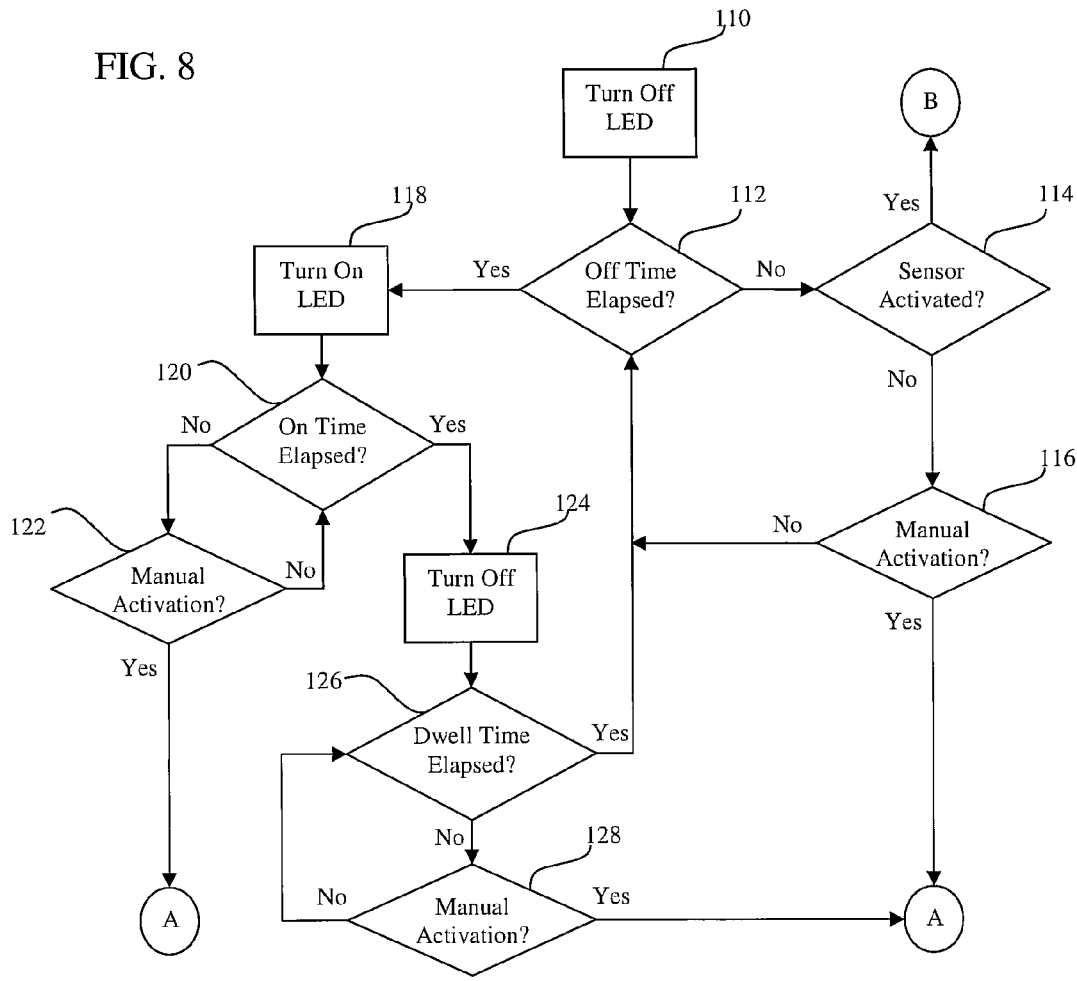
FIG. 8 is a flowchart that illustrates programming that may be executed during an active operational mode of the dispensing device of FIG. 3.

Turning to FIG. 8, the active operational mode of the device 26 begins at a block 110, which causes the LED 54 to be turned off. Thereafter, control passes to a decision block 112 to determine whether an "off-time" interval of the LED 54 has lapsed. In the present embodiment the "off-time" interval is preferably about 4.5 seconds. If the "off-time" has not lapsed control passes to another decision block 114, which determines if the phototransistor circuit 60 has detected the occurrence of a specified event. If it is determined that the phototransistor circuit 60 has detected the specified event, e.g., the entrance of a person into a room, control passes to the block 80 of FIG. 6 and the programming performs an activation sequence, as described above. However, if the phototransistor circuit 60 does not detect the specified event, control passes to a decision block 116 to determine whether an electronic signal has been generated by the depression of the pushbutton 38. Control passes to the block 82 of FIG. 6 to perform an activation sequence if the pushbutton 38 has been depressed or returns to the block 112 if the pushbutton 38 has not been depressed.

Referring again to block 112, upon the lapsing of the "off-time" interval control passes to a block 118. Block 118 causes the LED 54 to be turned on and passes control to a decision block 120. The decision block 120 determines whether an LED "on-time" interval has lapsed. In the present embodiment the "on-time" interval is preferably about 150 ms. If the "on-time" interval has not lapsed control passes to a decision block 122 to determine whether the pushbutton 38 has been depressed. Control passes to the block 82 of FIG. 6 to perform an activation sequence if the pushbutton 38 has been depressed or returns to the block 120 if the pushbutton has not been depressed. Upon expiration of the "on-time" interval control passes to a block 124, whereupon the LED 54 is turned off. Thereafter, control passes to a decision block 126, which determines whether a "dwell time" interval has lapsed. In the present embodiment the "dwell time" interval is preferably about 450 ms. If the "dwell time" interval has not lapsed control passes to a decision block 128 to determine whether the pushbutton 38 has been depressed. Control passes to the block 82 to perform an activation sequence if the pushbutton 38 has been depressed or returns to the block 126 if the pushbutton 38 has not been depressed. Upon expiration of the "dwell time" interval control passes back to the block 112 and the active operational mode repeats itself in a similar manner as described above.

The active operational mode causes the LED 54 to be alternatively turned on and off, i.e., to flicker. The flickering LED 54 allows a user to determine that the device 26 is in the active operational mode. Alternatively, any lighting methodology or other indication means may be provided to indicate any of the operating modes of the device 26. Further, an additional benefit of the flickering LED 54 is that if the device 26 includes a light sensor, deactivation of the LED 54 during an active sensory mode precludes such light sensor from being falsely triggered by the LED 54.

Disclosed herein is a cost effective and practical solution to the various problems identified in relation to prior art devices that include sensors to detect environmental conditions. More specifically, a non-linear circuit element is coupled to a phototransistor to establish a bias point. A voltage level at the bias point varies non-linearly with respect to a current through the phototransistor due to the non-linear circuit element. Such a non-linear relation allows the phototransistor to operate effectively over a wide range of environmental conditions. Further, the bias point can be coupled to a band-pass filter to attenuate unwanted high frequency and low frequency components from the voltage at the bias point. Still further, the present disclosure provides for amplification stages that can be coupled to the bias point to amplify the voltage level at the bias point. Consequently, a device that utilizes the phototransistor 34 can be operated in a wide range of environmental conditions and can be tuned to detect only those environmental conditions of interest. Further, it is also contemplated that any such device may utilize any of the operational methodologies or structure described in Carpenter et al. U.S. patent application Ser. No. 11/725,402 or those known to one of skill in the art in conjunction with the phototransistor 34 described herein.

In the above description the sensor is generally described as a phototransistor that is adapted to detect motion in a space. However, any other type of photodetectors and motion detectors may be alternatively or additionally utilized, e.g., a photodiode, a photomultiplier tube, a passive infrared or pyroelectric motion sensor, an infrared reflective motion sensor, an ultrasonic motion sensor, or a radar or microwave radio motion sensor. Further, the sensor can be replaced or used in combination with any other type of known sensor, e.g., a heat sensor, a humidity sensor, or an odor sensor.

Other embodiments comprising various combinations of the individual features of each of the foregoing described embodiments are specifically included herein.

INDUSTRIAL APPLICABILITY

The dispensing devices described herein include sensors that are advantageously configured to detect environmental conditions in a wide range of environments.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A dispensing device, comprising:
   a dispenser configured to dispense a volatile material;
   a sensor configured to detect an environmental condition;
   a nonlinear circuit element coupled to the sensor to establish a bias point, wherein a voltage level at the bias point varies nonlinearly with respect to a current that flows through the sensor, and wherein the current that flows through the sensor represents the environmental condition; and
   a controller coupled to the bias point, wherein the controller controls the dispenser to dispense the volatile material in response to the environmental condition.

2. The dispensing device of claim 1, wherein the sensor is a photocell and the environmental condition is motion.

3. The dispensing device of claim 1, wherein the nonlinear circuit element includes one or more diodes.

4. The dispensing device of claim 3, wherein the nonlinear circuit element includes one or more transistors configured as diodes.

5. The dispensing device of claim 1, wherein the voltage level at the bias point varies logarithmically with respect to the current that flows through the sensor.

6. The dispensing device of claim 1, wherein the controller is a microcontroller that interprets the signal at the bias point to detect the environmental condition.

7. The dispensing device of claim 1, further comprising an actuator arm and an aerosol container that contains the volatile material, wherein the controller actuates the actuator arm to dispense the volatile material from the aerosol container.

8. A dispensing device, comprising:
a dispenser configured to dispense a volatile material;
a phototransistor;
a diode coupled to the phototransistor to establish a bias point, wherein a voltage level at the bias point varies nonlinearly with respect to a current that flows through the phototransistor;
a band-pass filter coupled to the bias point to attenuate high and low frequency conditions; and
a controller coupled to the bias point via the band-pass filter, wherein the controller controls the dispenser to dispense the volatile material in response to a fluctuation in the voltage level at the bias point.

9. The dispensing device of claim 8, further comprising two diodes coupled in series with the phototransistor.

10. The dispensing device of claim 9, wherein one or both of the two diodes is a transistor configured as a diode.

11. The dispensing device of claim 8, wherein the band-pass filter includes a high-pass filter that includes at least one capacitor and a low-pass filter that includes at least one capacitor and at least one resistor.

12. The dispensing device of claim 8, further comprising one or more amplification stages that amplify the voltage at the bias point.

13. The dispensing device of claim 12, wherein the one or more amplification stages include one or more transistor gain stages.

14. The dispensing device of claim 8, wherein the fluctuation in the voltage level corresponds to a detection of motion.

15. The dispensing device of claim 8, further comprising at least one LED, wherein the controller controls the emission of light from the LED.

16. A method of dispensing a volatile material, comprising the steps of:
detecting an environmental condition with a photocell;
coupling a nonlinear circuit element to the photocell to establish a bias point therebetween, wherein a voltage level at the bias point varies nonlinearly with respect to a current that flows through the photocell; and
dispensing a volatile material in response to a transition in the voltage at the bias point.

17. The method of claim 16, further comprising the step of filtering high and low frequency conditions from the voltage level at the bias point.

18. The method of claim 17, further comprising the step of amplifying the voltage level at the bias point.

19. The method of claim 16, wherein the nonlinear circuit element includes one or more diodes coupled in series with the photocell.

20. The method of claim 19, wherein at least one of the one or more diodes is a transistor configured as a diode.

* * * * *